United States Patent [19]

Scott, Jr.

[11] 4,274,398
[45] Jun. 23, 1981

[54] SURGICAL RETRACTOR UTILIZING ELASTIC TUBES FRICTIONALLY HELD IN SPACED NOTCHES

[76] Inventor: Frank B. Scott, Jr., 6720 Bertner, Houston, Tex. 77030

[21] Appl. No.: 38,469

[22] Filed: May 14, 1979

[51] Int. Cl.³ .............................................. A61B 17/02
[52] U.S. Cl. ................................................... 128/20
[58] Field of Search ...................... 128/20, 12, 13, 15, 128/17, 18, 327

[56] References Cited

U.S. PATENT DOCUMENTS

| | | | |
|---|---|---|---|
| 1,400,616 | 12/1921 | McCrory et al. | 128/20 |
| 2,384,304 | 9/1945 | Helfrick | 128/20 |
| 2,845,925 | 8/1958 | Jayle | 128/20 |
| 3,168,093 | 2/1965 | Gauthier | 128/20 |
| 3,509,873 | 5/1970 | Karlin et al. | 128/20 |
| 3,515,129 | 6/1970 | Truhan | 128/20 |
| 3,542,015 | 11/1970 | Steinman | 128/20 |
| 3,762,401 | 10/1973 | Tupper | 128/20 |
| 3,823,709 | 7/1974 | McGuire | 128/20 |
| 3,910,280 | 10/1975 | Talonn | 128/327 |
| 3,970,075 | 7/1976 | Sindelar et al. | 128/20 |

OTHER PUBLICATIONS

Izmailov et al., "Universal Retractor for Cavity Surgery", Biomed. Engr., vol. 8, No. 5 (Sep.-Oct. 1974).

Primary Examiner—Kyle L. Howell
Assistant Examiner—J. L. Kruter

[57] ABSTRACT

A surgical retractor, which includes a frame conformed to fit the surface contour of the portion of the body to be operated on and at least one stay which includes an elastic member and tissue holding means. The frame has a plurality of notches spaced about its periphery and the elastic member of the stay is adapted to be inserted into one of the notches and held in place by friction to retract the tissue.

1 Claim, 5 Drawing Figures

SURGICAL RETRACTOR UTILIZING ELASTIC TUBES FRICTIONALLY HELD IN SPACED NOTCHES

BACKGROUND OF THE INVENTION

A. Field of the Invention

This invention relates to surgical apparatus, and more particularly to retractors.

B. Background of the Invention

During the course of a surgical procedure, the wound is separated and retracted by means retractors or stay sutures, which are generally held by trained assistants. Current retractors retract the wound in a non-yielding manner such that manipulation and movement by the surgeon as well as movement caused by contracting muscles or tissues of the patient result in bruising or tearing of the tissues. Once the wound is separated and retracted, further stabilizing, retracting, or delivering of exposed tissues or organs, require the placement of additional retractors or stay sutures which, again, must generally be held by trained assistants. Some organs are sufficiently mobile, for example, the eye, kidney, or bladder, that there are no retractors which fit the organ without the distortion thereof. Such organs require multiple stay sutures, which require excessive time and expense in the repeated placement, retraction, fixation, holding and often untangling of the stays.

SUMMARY OF THE INVENTION

It is an object of the present invention to provide a retractor which overcomes the shortcomings of the prior art. More specifically, it is an object of the present invention to provide a retractor that decreases or eliminates the need for trained people to retract tissue at the direction of the surgeon. It is a further object of the present invention to provide a retractor that allows the surgeon to quickly and repeatedly adjust the retraction, delivery, fixation, and exposure of various parts of the wound and its contents as the operation progresses.

Briefly stated, the foregoing and other objects of the present invention are achieved by providing a retractor that includes a generally annular frame conformed to fit the surface contour of the portion of the body to be operated upon. A plurality of stays are provided, which are adapted to be inserted into and held in place in a plurality of notches spaced about the periphery of the frame. The stays include a tissue holding device, for example, a hook, and an elastic member. The surgeon can adjust quite precisely the traction applied to the tissue by the placement of the elastic member within the slots. Also, the surgeon can quickly readjust both the direction and force of the traction quickly and easily.

DESCRIPTION OF THE PREFERRED EMBODIMENT

Figure 1:
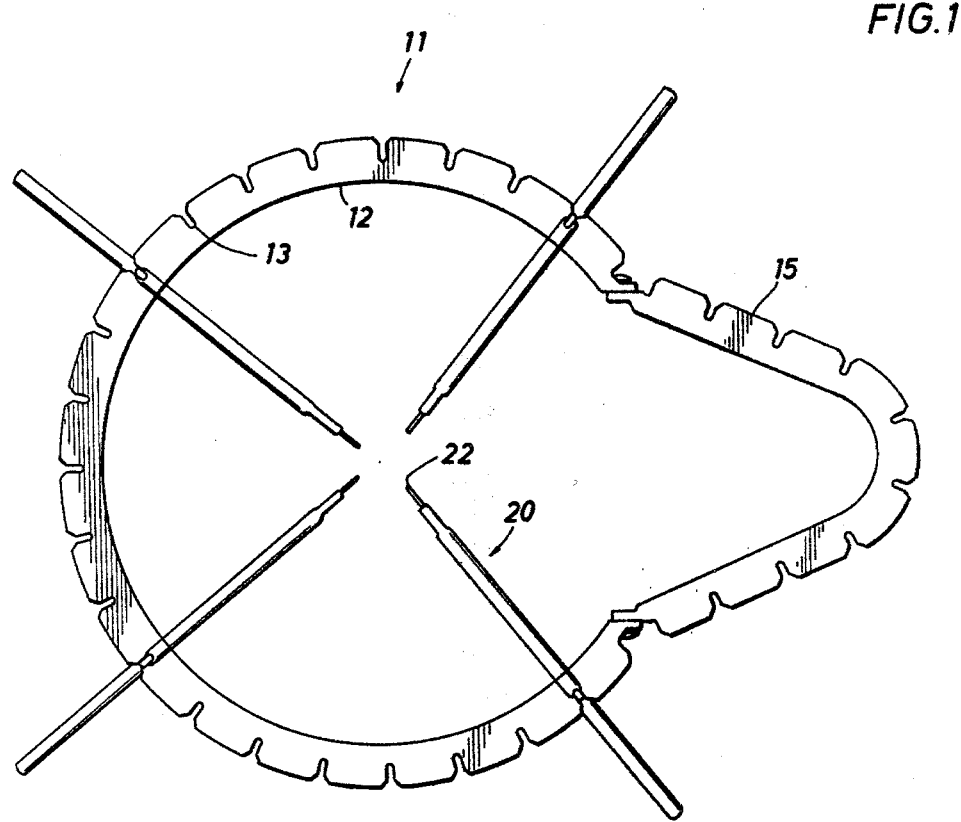
FIG. 1 is a top view of one preferred embodiment of the present invention, which illustrates a retractor adapted for use in the genitourinary area.

Referring now to the drawings, the retractor of the present invention is designated generally by the numeral 11. Retractor 11 includes a generally annular frame 12 and a plurality of stays, each designated generally by the numeral 20.

Figure 3:
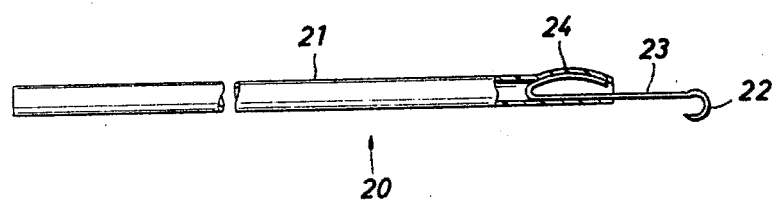
FIG. 3 is a side view of the stay of the present invention.

Referring to FIG. 3, each stay 20 includes an elastic member 21 that is connected to a tissue-holding device, which in the preferred embodiment is a hook 22. In the preferred embodiment, elastic member 21 comprises a section of silicon rubber tubing. Hook 22 includes a shank portion 23 and a recurved handle portion 24. In the manufacture of stay 20, an end of elastic member 21 is soaked in xylene until the end becomes malleable, whereupon handle portion 24 is inserted thereinto. When the xylene evaporates from elastic member 21, the tubing again becomes elastic and holds handle portion 24 firmly in place. The shape of handle portion 24 provides a convenient means by which the surgeon can manipulate hook 22.

Figure 2:
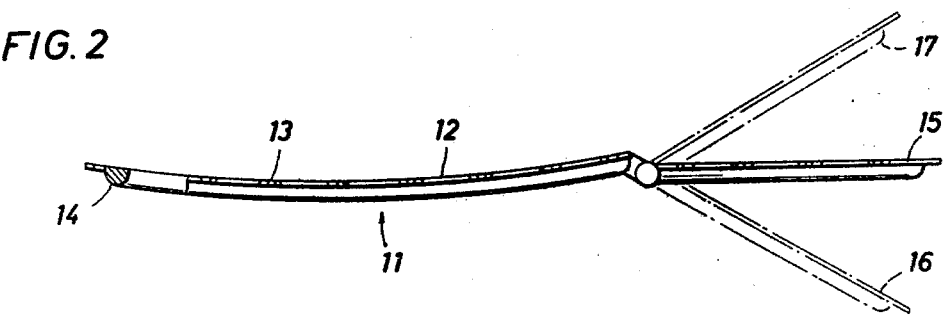
FIG. 2 is a side view of the retractor of FIG. 1.
Figure 4:
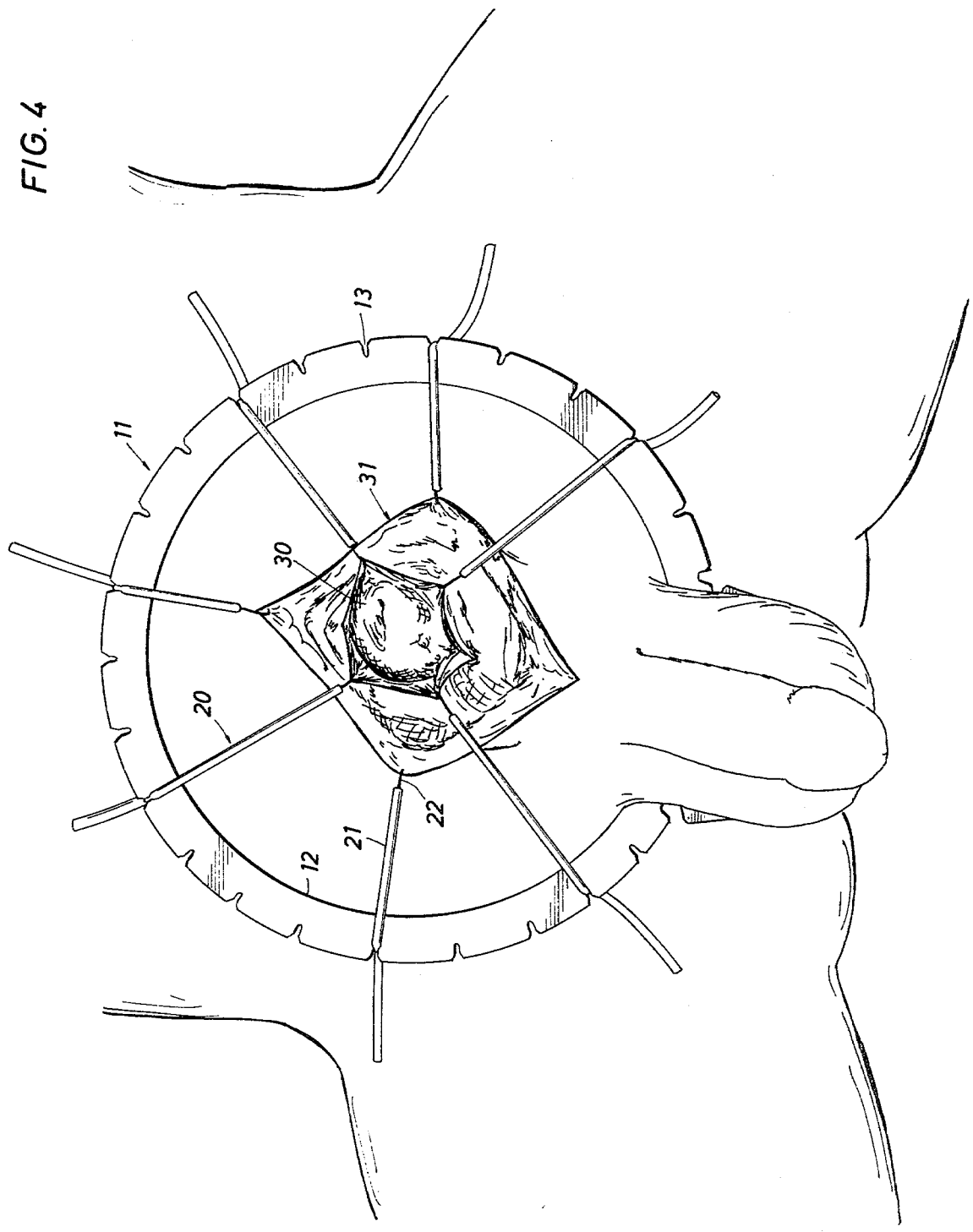
FIG. 4 is a view showing the retractor of FIG. 1 in use in performing a bladder operation.

Referring now to FIGS. 1 and 2, frame 12 is formed from a non-yielding material, as for example stainless steel, and is conformed to fit the surface contours of the portion of the body to be operated upon, as for example the genitourinary area as shown in FIG. 4. Frame 12 has a plurality of notches 13 about the periphery thereof. The width and depth of each notch 13 is such that elastic portion 21 of stay 20 may be inserted therein and held in place by friction without damaging elastic member 21. Frame 12 includes a spacer portion 14 around the lower side thereof, which spaces notches 13 from the body to allow the surgeon easier access thereto.

A portion, designated by the numeral 15, is hingedly connected to frame 12 so that the shape of frame 12 may be changed, as shown in FIG. 2. Portion 15 may be lowered to the position designated by the numeral 16 in FIG. 2 when retractor 11 is used as illustrated in FIG. 4. Portion 15 may be raised to the position designated by the numeral 17 in FIG. 2 when retractor 11 is used in the scrotal approach technique in implantation of a penile prosthesis.

Figure 5:
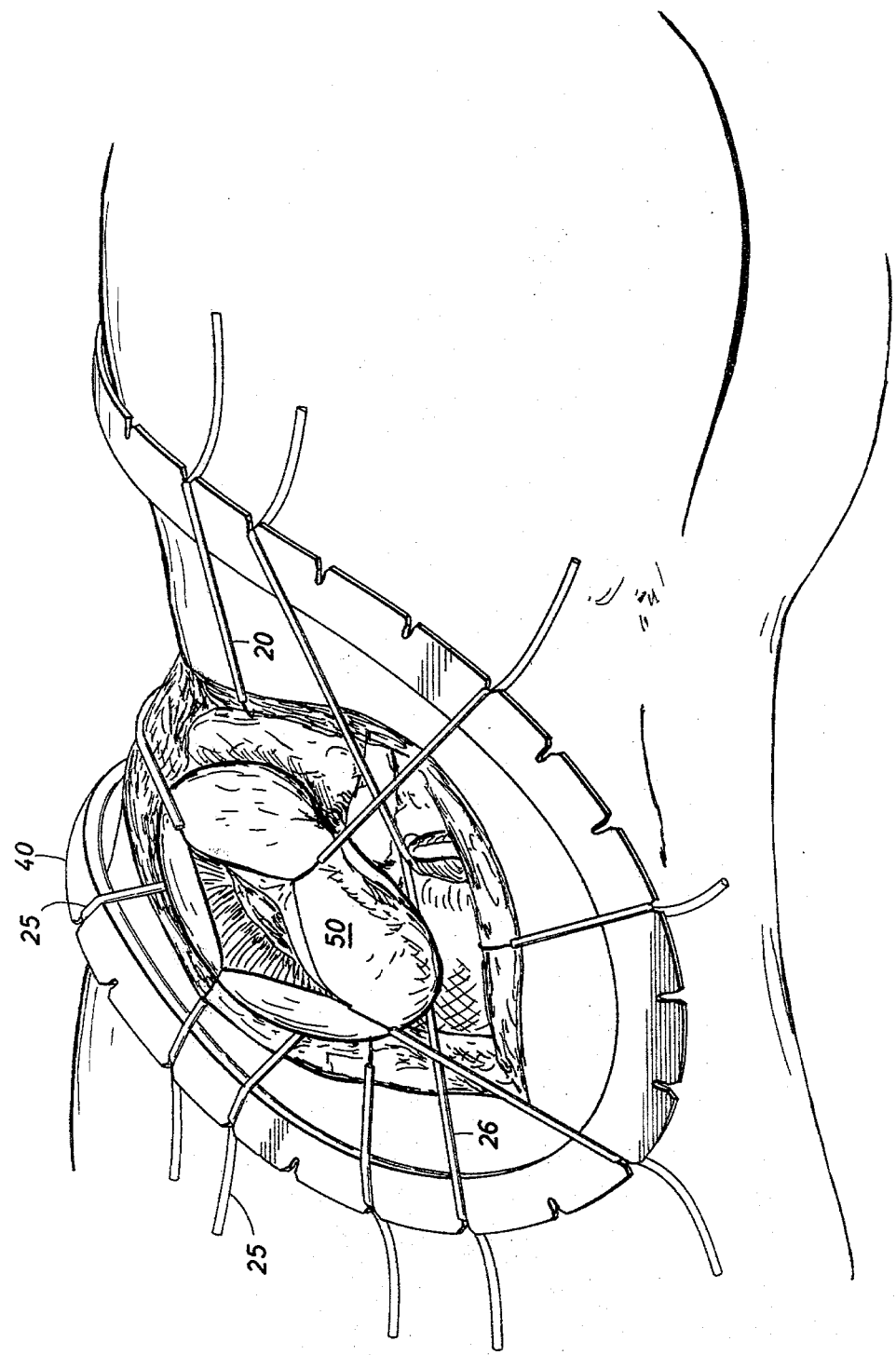
FIG. 5 is a view of another embodiment of the present invention in use to perform a kidney operation.

The operation of the retractor of the present invention may be understood by referring to FIGS. 4 and 5. FIG. 4 illustrates the use of retractor 11 to expose the bladder 30. The surgeon would first place frame 12 as shown. After making his initial incision, the surgeon would use a pair of stays 20 to open the wound designated generally by the numeral 31. The surgeon can control the tension applied to the edges of the wound by his placement of stays 20 in notches 13. As the surgeon proceeds through deeper layers of tissue, wound 31 is pulled further open by the tension of elastic members 21, and if the direction or force or direction of the tension that is necessary needs to be changed, the surgeon can quickly do so simply by removing and reinserting hook 22 and/or by moving elastic member 21 to a different notch.

A further example of the use of the retractor of the present invention is shown in FIG. 5, which illustrates a kidney operation. A frame 40 is provided to conform to the right flank. Again, a plurality of stays 20 would be used to open the wound and thereby expose the kidney 50. FIG. 5 illustrates further the versatility of the retractor of the present invention. For example, a section of tubing, designated by the numeral 25, may be looped under the kidney to suspend and to deliver the kidney to the surgeon for greater ease in operating thereon. Additionally, another section of tubing, designated by the numeral 26, could be used as a tourniquet to halt the flow of blood to the kidney.

From the foregoing, it can be seen that the retractor of the present invention increases greatly the efficiency and effectiveness of the surgeon. At least one member of the surgical team is eliminated, thereby reducing the expense to the patient. Moreover, by eliminating the need for an assistant directed by the sugeon, the surgeon is able to proceed more quickly, which results in further cost savings. Also, substantial benefits to the physical wellbeing of the patient are achieved by the use of the retractor of the present invention. The precise control that the surgeon has over the placement of and tension applied to the retracting devices minimize trauma during the course of the operation.

Further modifications and alternative embodiments of the retractor of this invention will be apparent to those skilled in the art in view of this description. Accordingly, this description is to be construed as illustrative only and is for the purpose of teaching those skilled in the art the manner of carrying out the invention. It is to be understood that the forms of the invention herewith shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. A surgical retractor for use in performing surgery upon a portion of the body having a surface contour, which comprises:
    a generally annular frame conformed to fit the surface contour of the portion of the body to be operated upon, said frame having a periphery, said periphery having a plurality of notches having a width and depth spaced thereabout;
    a stay which includes an elastic member having a length and a width and tissue holding means attached thereto, wherein the width of said elastic member is greater than the width of said notches such that said elastic member is held in place by friction when inserted into one of said notches; and
    said elastic member includes a section of elastic tubing and said tissue holding means including a hook having a handle portion inserted in said tubing.

* * * * *